US010098623B2

(12) United States Patent
Vogtherr et al.

(10) Patent No.: US 10,098,623 B2
(45) Date of Patent: Oct. 16, 2018

(54) SURGICAL DEVICE FOR STABILIZING OR IMMOBILIZING MOVING TISSUE

(71) Applicant: Aesculap AG, Tuttlingen (DE)

(72) Inventors: Robert Vogtherr, Tuttlingen (DE); Dominik Seyfried, Königsfeld (DE); Andreas Elisch, Schramberg (DE); Thomas Beck, Durchhausen (DE); Michele Genoni, Zürich (CH); Dieter Weisshaupt, Immendingen (DE); Pedro Morales, Tuttlingen-Nendingen (DE)

(73) Assignee: Aesculap AG, Tuttlingen (DE)

( * ) Notice: Subject to any disclaimer, the term of this patent is extended or adjusted under 35 U.S.C. 154(b) by 234 days.

(21) Appl. No.: 14/774,858

(22) PCT Filed: Mar. 14, 2014

(86) PCT No.: PCT/EP2014/055172
§ 371 (c)(1),
(2) Date: Sep. 11, 2015

(87) PCT Pub. No.: WO2014/140316
PCT Pub. Date: Sep. 18, 2014

(65) Prior Publication Data
US 2016/0030031 A1 Feb. 4, 2016

(30) Foreign Application Priority Data
Mar. 14, 2013 (DE) .................. 10 2013 102 628

(51) Int. Cl.
A61B 17/02 (2006.01)
A61B 17/00 (2006.01)
(Continued)

(52) U.S. Cl.
CPC .......... *A61B 17/0218* (2013.01); *A61B 17/02* (2013.01); *A61B 2017/0046* (2013.01);
(Continued)

(58) Field of Classification Search
CPC .......... A61B 2017/00323; A61B 2017/00411; A61B 2017/00535–2017/00544
See application file for complete search history.

(56) References Cited

U.S. PATENT DOCUMENTS 3,858,578 A 1/1975 Milo
5,662,300 A 9/1997 Michelson
(Continued)

FOREIGN PATENT DOCUMENTS

CN 101366645 A 2/2009
CN 101703423 A 5/2010
(Continued)

OTHER PUBLICATIONS

Chinese Office Action with English language translation for Application No. 201480015488.3, dated Apr. 26, 2017, 19 pages.
(Continued)

*Primary Examiner* — Thaddeus Cox
(74) *Attorney, Agent, or Firm* — RatnerPrestia

(57) ABSTRACT

A surgical device for stabilizing or immobilizing moved tissue or for positioning organs, especially a part of a beating heart, includes a flexible arm, especially a link arm, fixed or fixable to a base member which arm can be brought into different positions and/or attitudes and at the free end of which at least one retaining element is arranged, and comprising a tightening mechanism by which the arm can be fixed at a desired position. The tightening mechanism is tightened and/or released by means of a manually controllable external power source.

15 Claims, 12 Drawing Sheets

(51) Int. Cl.
  *A61B 90/57* (2016.01)
  *A61B 90/50* (2016.01)
(52) U.S. Cl.
  CPC ............... *A61B 2017/00314* (2013.01); *A61B 2017/00323* (2013.01); *A61B 2017/00411* (2013.01); *A61B 2017/00535* (2013.01); *A61B 2017/0243* (2013.01); *A61B 2090/508* (2016.02); *A61B 2090/571* (2016.02)

(56) References Cited

U.S. PATENT DOCUMENTS

| | | | |
|---|---|---|---|
| 6,581,889 B2 | 6/2003 | Carpenter | |
| 6,632,170 B1* | 10/2003 | Bohanan | A61B 90/50 403/83 |
| 6,866,628 B2 | 3/2005 | Goodman | |
| 7,311,664 B2 | 12/2007 | Goodman | |
| 7,399,272 B2 | 7/2008 | Kim | |
| 7,476,196 B2 | 1/2009 | Spence | |
| 7,479,104 B2 | 1/2009 | Lau | |
| 8,114,118 B2 | 2/2012 | Knodel | |
| 2002/0058860 A1* | 5/2002 | Muhanna | A61B 90/50 600/227 |
| 2003/0083555 A1 | 5/2003 | Hunt et al. | |
| 2003/0216619 A1 | 11/2003 | Scirica | |
| 2006/0004250 A1* | 1/2006 | Parihar | A61B 90/50 600/37 |
| 2006/0030889 A1 | 2/2006 | Ben-Haim | |
| 2008/0103491 A1 | 5/2008 | Omani | |
| 2008/0214925 A1 | 9/2008 | Wilson | |
| 2010/0178100 A1* | 7/2010 | Fricke | F16C 11/106 403/90 |
| 2012/0157788 A1* | 6/2012 | Serowski | A61B 17/0206 600/229 |
| 2012/0253116 A1 | 10/2012 | Sniffin | |
| 2013/0178869 A1* | 7/2013 | Marczyk | A61B 19/20 606/130 |

FOREIGN PATENT DOCUMENTS

| | | |
|---|---|---|
| DE | 10357105 | 4/2005 |
| DE | 202009006971 | 9/2009 |
| DE | 202009007202 | 9/2009 |
| EP | 0808606 | 11/1997 |
| GB | 911419 | 11/1962 |
| JP | 2005507702 A | 3/2005 |
| WO | 0150946 | 7/2001 |
| WO | 2011159733 | 12/2011 |

OTHER PUBLICATIONS

German Search Report for German Application No. 10 2013 102 628.1 dated Dec. 12, 2013, with partial translation.
International Search Report for International Application No. PCT/EP2014/055172 dated Oct. 9, 2014.
Notification of Reasons for Rejection for Japanese Application No. 2015-562217, dated Nov. 28, 2017, including English translation, 10 pages.

* cited by examiner

SURGICAL DEVICE FOR STABILIZING OR IMMOBILIZING MOVING TISSUE

RELATED APPLICATIONS

This is the U.S. National Phase entry of International Application No. PCT/EP2014/055172, filed Mar. 14, 2014, which claims the benefit of priority of German Application No. DE 10 2013 102 628.1, filed Mar. 14, 2013. The contents of International Application No. PCT/EP2014/055172 and German Application No. DE 10 2013 102 628.1 are incorporated by reference herein in their entirety.

FIELD

The present invention relates to a surgical device for stabilizing or immobilizing a part of moving tissue or else for positioning organs or surgical instruments and apparatuses during operation as well as to a surgical link arm for said device.

BACKGROUND

There are different types of surgical interventions in which the operating surgeon has to work on moving organs of the human body. This is the case, for example, in a coronary artery bypass graft (CABG) surgery on the beating heart. In such bypass graft surgery, a portion of a contracted coronary artery has to be bypassed using a graft vessel, wherein the vessel is sewed to the artery at two positions. Therefore, this operation is frequently carried out using a heart-lung machine under cardioplegia. As soon as the intervention is completed, the heart is made to beat again. This operation can also be carried out without a heart-lung machine while the heart is beating. As a matter of course, an operation on a beating heart is by far more difficult for the operating surgeon to perform than an operation on a non-beating heart. Therefore devices for stabilizing and immobilizing a part of the heart are required.

One type of stabilizing device is based on the vacuum principle. It includes elements which are attached to a part of the heart and fixed in place by means of a vacuum. The entire device comprises a stationary part which is usually fixed to a rib spreader, a flexible arm consisting of a plurality of individual elements, an actuating element by which said arm is tightened, and one or more vacuum elements to which a vacuum hose is connected. In said arm, a pull rope is provided which is mechanically braced by means of the actuating element. The pull rope is tightened via a worm or an eccentric gear. Said devices are known, for example, from the documents U.S. Pat. No. 6,866,628 B2, U.S. Pat. No. 7,311,664 B2, U.S. Pat. No. 7,399,272 B2, U.S. Pat. No. 7,476,196 B2 or U.S. Pat. No. 7,479,104 B2.

The second type of stabilizing device functioning without a vacuum is very similar. In this case, the technology consists of the same components except for the vacuum elements. Instead of vacuum elements, in this case there are inoperable, inactive elements, such as fork-like stabilizing elements, that are pressed onto part of the heart so as to stabilize that part of the heart purely mechanically. This technology is described, for instance, in U.S. Pat. No. 6,581,889 B2.

It is a drawback of the previous solutions that with all common devices the user has to work with both hands for this type of procedure. At the proximal end, the user arrests the flexible arm by means of the operating element provided for this purpose, while he/she guides the distal end and presses it onto the tissue. This operating step is further complicated by the flexible link arm having at its proximal end a pivot axis by which it can be pivoted in the horizontal plane toward the stationary part attached to the spreader. This pivot axis in many cases is locked simultaneously with the arm by means of the same pull rope. In extreme cases, the user may require an assistant, for example for retaining the pivot axis at the desired position during the locking operation.

Moreover, with these devices, it is frequently not defined how strongly the pull rope is tightened. Different users will operate the actuating element, which frequently is a screw mechanism, differently depending on their own sense of feel and strength, and thus will generate both different tensile forces and different rigidities of the link arm.

Another drawback resides in the high cost for using such a device. Due to the fact that the individual arm segments and the pull rope consisting of plural single strands to ensure flexibility are difficult to clean in an efficient manner, the entire instrument is not re-usable and is used only once.

SUMMARY

It is the object of the present invention to provide a surgical device for stabilizing or immobilizing moving organs which does not suffer from the afore-described drawbacks. In particular, a device is to be provided which facilitates the handling, especially single-handed operation, by an operating surgeon. Furthermore, the operability of the device should be independent of a particular person. Finally, the operating costs for using the device should be reduced.

A surgical device according to the invention by which moving tissue can be stabilized, immobilized or retained, or organs can be positioned, e.g. part of a beating heart during coronary artery bypass graft surgery, includes a base member to which a flexible arm, e.g. in the form of a link arm, is fixed or fixable. Said link arm can be brought into different positions and/or attitudes. At least one retaining member is arranged at a free end of the link arm, by which the respective tissue or organ can be retained and/or stabilized. The link arm can be immobilized at a desired position via a tightening mechanism. In accordance with the invention, tightening and/or releasing of the tightening mechanism and immobilizing and releasing the link arm are performed by means of a power source.

Hence tightening and/or releasing of the flexible arm is not performed purely mechanically, as in the afore-mentioned devices, by applying manual force, but is power completely by, or at least assisted by, a hydraulic, pneumatic or electric power source. This facilitates a single-handed operation of the device, as the surgeon does not have to manually tighten and/or release the tightening mechanism, for which purpose he/she usually needs both hands, i.e. one for holding the device and the other for tightening and/or releasing. By the single-handed operation the flexible arm can be easily positioned and arrested and assists the operating surgeon e.g. in stabilizing tissue or in positioning organs.

Another advantage of an energy or power source consists in the fact that the tightening or releasing force can be adjusted more accurately and the tightening mechanism is constantly tightened with the same tightening force and therefore does not vary depending on the respective operating person. Hence, it can be ensured that the fixed or locked arm always has the desired optimum rigidity and provides retaining force and is not tightened in a too weak or too strong manner depending on the user. The former case might entail the fact that the arm yields during operation or releases the tissue or organ to be retained, and the latter might result in excessive tightening and destroying the tightening mechanism and thus in the uselessness of the device.

The link arm offers a plurality of further applications such as for retaining surgical hooks or spatulas in the field of neurosurgery or as a flexible retaining arm for retaining and positioning further equipment such as a trocar or a camera for implementing or assisting in a surgical intervention. The retaining element of the link arm may be provided with a universal adapter to enable the connection of various single-use or re-usable surgical instruments and devices which are retained and positioned by means of the link arm during surgical intervention.

The power source can be an external power source provided outside the surgical device. This is advantageous when the surgical device and especially the base member are to be designed in a space-saving manner. The external arrangement of the power source can also be of advantage when an exchangeable energy storage unit is provided as power source. Then the external arrangement especially facilitates the exchange of a used-up energy storage unit.

The power source used for tightening and/or releasing the tightening mechanism can be controlled or activated by one or more manually operable actuating elements. When the actuating element is provided on the distal side of the link arm, i.e. close to the retaining element, this offers the advantage that the surgeon can position the retaining element single-handedly at the respective tissue or organ and can simultaneously fix it in the desired position via the actuating element and, conversely, can release it after completed surgical intervention and remove it from the tissue and/or organ. In the prior art devices mentioned in the beginning the link arm is fixed by means of a rotary knob arranged at the proximal end of the link arm which is appropriately distant from the actual operation site. However, it is advantageous when the power source can also be controlled, apart from the distal actuating element, via an actuating element arranged at the proximal side of the link arm. If the retaining element is immersed so deeply in the patient's body cavity that the distal actuating element cannot be reached or is difficult to reach, the user can release and, if appropriate, newly position the arm by the actuating element on the proximal side of the link arm provided outside the patient. This permits flexible use of the surgical device. Alternatively, the actuating element provided on the base member can also constitute the only actuating element.

In accordance with an additional or alternative aspect of the invention, the tightening mechanism can be tightened and released and the link arm can be fixed and released in different ways. On the one hand, the tightening mechanism can be tightened by means of external power and the tightening mechanism can be manually released or vice versa, on the other hand two different energies can be used for releasing and tightening the tightening mechanism. In addition or alternatively, the tightening mechanism can be configured so that the tightening mechanism is tightened automatically, i.e. without any effort on the user's part, and the tightening mechanism is released by controlling or activating a power source. In this way the tightening mechanism can be tightened by means of spring force so that the tightening mechanism tightens and fixes the link arm at the respective position and the user can release and render the link arm flexible by appropriately controlling the power source. The advantage of the spring bias is in particular that by the spring force a so-to-speak continuous force is provided over a certain travel and this force ensures the same optimum bias of the tightening mechanism and the optimum rigidity of the arm in each application. It is another advantage of the automatic biasing of the tightening mechanism, e.g. by a spring, that the tightening mechanism has to be operated by the user merely for release and automatically remains in its locked position, when the user releases the device and the appropriate actuating member for controlling the power source.

According to an additional or alternative aspect of the invention, the tightening mechanism includes one or more pull ropes which are guided through a plurality of link elements of the link arm which are movable relative and especially complementary to each other and by which the link elements can be braced against each other in frictional fit. An appropriate actuating mechanism being connected to the pull rope and either tightening or releasing the same can be operated via the power source.

The actuating mechanism according to the invention converts the power supplied by the power source to a corresponding mechanical force for operating the pull rope.

The power source can be of any type as long as it provides energy which is suited and sufficient for operating the pull mechanism in at least one direction. The power source can be a hydraulic or pneumatic pressure source, the actuating mechanism can be a hydraulically or pneumatically operable cylinder-piston mechanism and a fluid control element, e.g. a valve or a valve arrangement, can be controlled by the at least one actuating element for controlling the fluid pressure acting on the cylinder-piston mechanism. Also, the power source can be a storage device for electrical energy, especially a battery or an accumulator, the actuating mechanism can be a motor-actuated cylinder-piston mechanism and an electric or electronic control device for controlling an electric motor adapted to adjust the cylinder-piston mechanism can be controlled via the at least one actuating element. The electric motor is preferably provided, as the cylinder-piston mechanism, in the base member of the surgical device.

In accordance with an aspect of the invention, the pull rope of the pulling mechanism is biased by means of a spring acting on the cylinder-piston mechanism and is relaxed by compressed air from a compressed air source acting on the cylinder-piston mechanism, especially a compressed air cartridge or a standardized compressed air connection. The use of a compressed air cartridge offers the advantage that it permits completely autonomous working. Alternatively, the cylinder-piston mechanism can be connected to the air supply provided in each operating theater via a standardized compressed air connection and a hose or a line.

Hence, depending on the application, the surgical device can be connected to a compressed gas cartridge or a given compressed air source.

In accordance with an additional or alternative aspect of the invention, the control medium used for controlling the fluid control element and the working medium used for operating the cylinder-piston mechanism can be different. For example, the piston of the cylinder-piston mechanism can be operated with compressed air, while the control of the valve which makes the compressed air act on the compressed air piston or not is electrically controlled. The lines required for this purpose can be accommodated in a by far more space-saving manner between the actuating element and the fluid control element. Alternatively, also the same medium can be used as control and working medium, wherein, when compressed air is used for the control medium for controlling the valve, by far lower pressure than for the working medium can be used to operate the compressed air piston and thus the control lines can have by far thinner walls and can be more flexible and the entire actuating element can have a more compact design. In other configurations, also one power source can be sufficient.

The cylinder-piston mechanism which is preferably provided in the base member of the device is connected to the external control power sources and working power sources via appropriate connections and lines.

In accordance with an alternative aspect of the invention, the pull rope of the pulling mechanism is biased via a spring acting on the cylinder-piston mechanism and is relaxed by a force caused by the electric motor and acting on the cylinder-piston mechanism. The electric motor, which especially can also be a linear motor, draws its energy from an electric power source, especially from an electrical connection or alternatively or additionally from an energy storage unit such as a battery or an accumulator. The use of an energy storage unit offers the advantage that it permits working completely autonomously. As an alternative, the electric motor for the cylinder-piston mechanism can be connected to the electrical power supply provided in every operating theater via a standardized electrical connection and a line.

The base member of the device can be adapted to be fastened to a retaining means provided in or at the operating site, especially a sternum spreader, via a fastening portion. When the retaining element is positioned against the tissue or the organ and the flexible arm is fixed by the tightening mechanism, the tissue or organ is retained in position by the retaining element, the fixed arm, the base member and the stationary retaining device.

In accordance with an aspect of the invention, the link arm can be rotatably supported relative to the base member and the retaining element can be pivoted relative to the link arm. Moreover, since the link arm is bendable in any direction, the retaining element can be brought into each desired position due to the diverse degrees of freedom. Preferably the pivoting capacity of the retaining element relative to the link arm and the rotatability of the link arm relative to the base member are suppressed or restricted, when the tightening mechanism is tightened so that not only the shape of the link arm but also the position of the retaining element relative to the link arm and the position relative to the base member are fixed.

When the actuating element for controlling the power source is on the distal side of the link arm and the fluid control element, the electric or electronic control device and the setting element for the actuating mechanism of the tightening mechanism are on the distal side of the link arm, especially in the base member, a control line has to lead from the actuating element to the fluid control element, the electric or electronic control device and the setting element. This signal or energy transmission lines can be provided inside or outside the link arm. Advantageously, the transmission lines extend through the interior of the link arm and thus are protected against external influences. In order to lead the lines through the interior of the link arm, each of respective link elements of the link arm can have a central pull rope passage for the pull rope and at least one eccentrically arranged recess for lines, especially for a control line between the distal actuating element and the fluid control element and the electric or electronic control device. The separately formed recesses for the lines ensure that the lines do not contact the pull rope of the tightening mechanism and mutually influence each other, respectively. Instead of providing the pull rope passage and the line recess in the link elements, alternatively each of the link elements can be provided with a separate centrally and rotatably supported rotary disk in which the pull rope passage and the line recess are provided. By the relative rotation of this rotary disk with respect to the link elements twisting among the link elements can be compensated which otherwise might result in damage of the lines. Alternatively, the link elements can be provided with an anti-rotation device, especially with engaging locking members so as to restrict twisting of the link elements around the pull rope. This variant, too, prevents damage of the control lines.

According to an aspect of the invention, the size of the link elements decreases with increasing distance from the base member and as a function of the course of the bending moment to be expected at the link arm so as to reach uniform bending of the arm.

According to an alternative aspect of the invention, the size of taper angles of tapered inner contact surfaces of the link elements increases with an increasing distance from the base member and as a function of the course of the bending moment to be expected at the link arm so as to reach uniform bending of the arm. The external dimensions of the link elements thus can be kept constant over the entire length of the link arm.

According to an aspect of the invention, the device can have a modular design, wherein the link arm and the base member can be connected to be mechanically releasable so that the link arm is used as exchangeable single-use module due to the difficulties of cleaning the individual link elements and the pull rope and the base member including the actuating mechanism and control elements of the power source is intended to be a re-usable engineering block. The interface between the link arm and the base member is configured so that, apart from the mechanical coupling, also a functional coupling is performed between the pull rope and a setting element of the tightening mechanism and, where appropriate, further interfaces such as control lines, electrical contacts etc. are connected. Re-usable components, i.e. the engineering block, entail a cost saving vis-à-vis comparable products. A substantial further advantage of the modular structure can be seen in the fact that the engineering block can be combined, depending on the application, with different functional ends or link arms having different sizes or different effectors or retaining elements.

According to an aspect of the invention, in a modular structure device, the power source or the energy storage unit is provided outside the base member. The power source or the energy storage unit can be inserted in the link arm or can be connected to the same. Alternatively, the energy storage unit can be fixedly integrated in the link arm and can be designed for single use.

According to an aspect of the invention, the power source in the form of a self-sustaining energy storage unit and the dismountable arm can be formed so that they can be interconnected. Such a configuration is advantageous when the respective connections of the arm and of the energy storage unit provided for the base member are orientated so that a combination of the arm and the energy storage unit can be mounted or connected to the base member by one single movement or by one single manipulation.

If the connection between the arm and the energy storage unit is configured to be fixed, and if the energy stored by the energy storage unit can only be exploited between the first mounting of the fixed arm-energy storage combination on the base member and the first dismounting of the fixed arm-energy storage combination from the base member, then safety is improved. In this context, the term fixed means that it is not releasable or releasable only with great effort and especially not without using tools. If the dismountable arm is not intended to be repeatedly used for reasons of hygiene, it is advantageous to render the arm usable for single use only. This is ensured, according to this aspect of the invention, by the fact that the energy storage unit can transmit energy to the base member only after the first connection to the base member and that, with the change of the energy storage unit, the fixed connection between the energy storage unit and the arm also requires the change of the arm. The fact that the energy can only be used between the first connection and the first disconnection of the energy storage unit is accomplished by a sealing membrane, when the energy storage unit is a compression cartridge, and by means of a discharge mechanism, when the energy storage unit is an electrical energy storage unit.

When the power source to be connected, such as a compressed gas cartridge, a battery, an accumulator, a hose or a line, are unsterile and therefore cannot be directly connected to the base member of the device located in direct vicinity of the operating site, according to a different aspect of the present invention, an adapter unit is interconnected between the base member and the power source, which adapter unit forms the separation between the sterile region and the unsterile region and which is connected, on the one hand, via detachable lines to the base member and, on the other hand, to the power source.

In accordance with an aspect of the invention, parts of the setting or control elements, especially those requiring more space than provided by the base member with a compact design, can be provided in the adapter unit.

Another aspect of the present invention relates to a surgical working arm for stabilizing or immobilizing moving tissue or for positioning organs, especially a part of a beating heart, which can especially be used in a surgical device according to the invention. Such working arm includes a flexible link arm adapted to be brought into different positions and/or attitudes and comprising a plurality of strung link elements movable relative to each other and especially being complementary and at least one retaining element arranged at the distal end of the link arm. In accordance with the invention, furthermore a coupling portion is provided for mechanical and functional connection of the working arm to a surgical device, wherein a pull rope which is guided through the link elements and by which the link elements can be frictionally braced against each other includes a proximal connecting portion adapted to be connected, especially by form fit without the use of tools, to a tightening mechanism provided in the surgical device or an engineering block of a surgical device.

This working arm or working arm module can be inexpensively manufactured and includes no cost-intensive setting elements or equivalents for the tightening mechanism, but merely provides interfaces for the connection thereto. Thus, this working arm can be provided for single use. Furthermore, different types of such working arm can be provided for use with the same engineering block as long as an identical or standardized coupling portion is used.

The surgical working arm may further include an actuating element provided at the distal end of the link arm for controlling the tightening mechanism provided in the surgical device and control lines connecting the actuating element to interfaces which are provided in the coupling portion for transmission of the control signals or instructions to the surgical device. The control lines can extend outside, but preferably inside the link arm.

Further advantages and configurations of the device according to the invention will be evident from the following description of preferred embodiments of the invention.

BRIEF DESCRIPTION OF THE DRAWINGS

FIG. 12b shows a detail of FIG. 12a;

FIG. 13b shows a detail of FIG. 13a;

DETAILED DESCRIPTION

Figure 1:
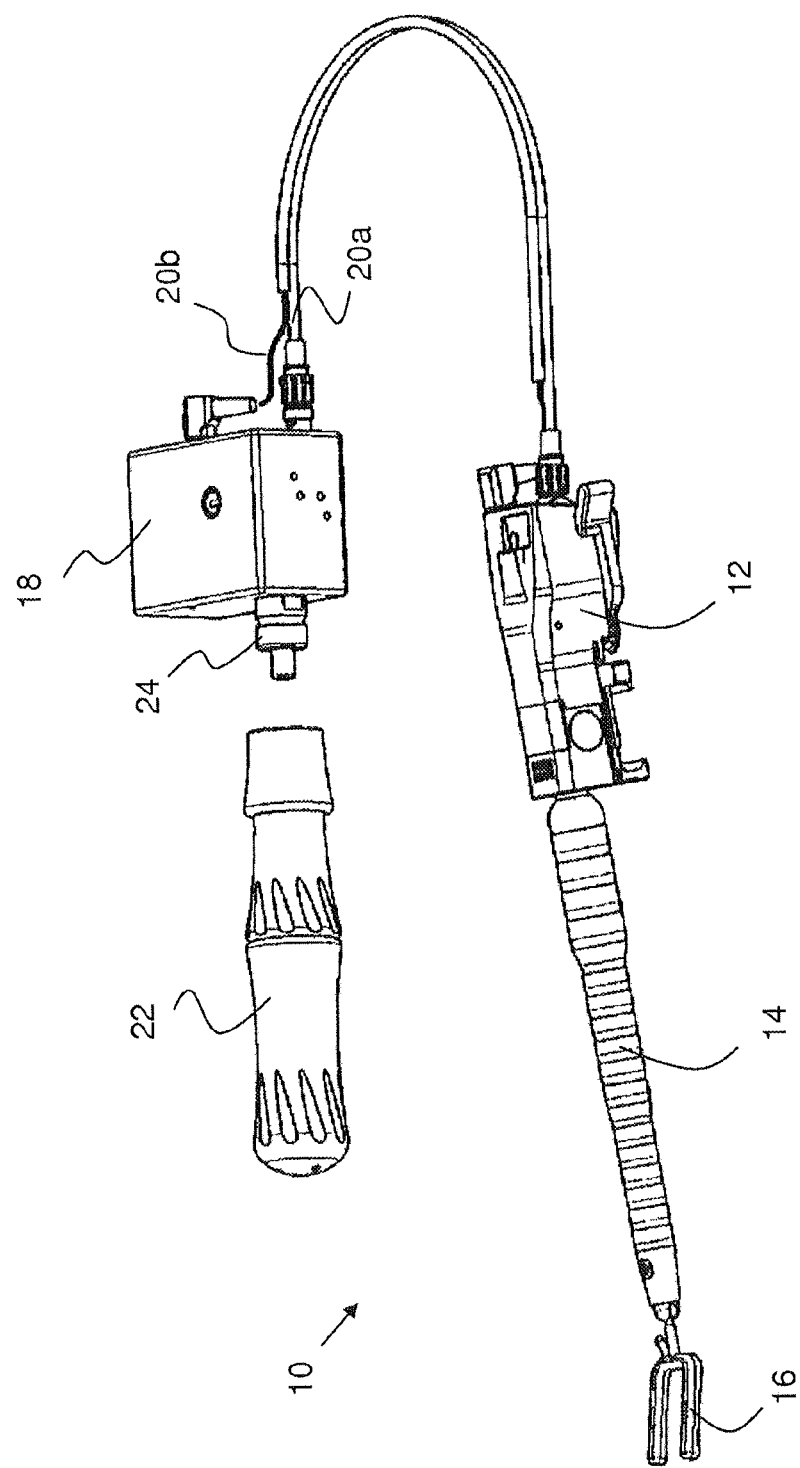
FIG. 1 shows a perspective view of a surgical device according to a first embodiment of the invention.

FIG. 1 illustrates a perspective view of a surgical device 10 for stabilizing or immobilizing a part of a moving tissue or else for positioning organs according to a first embodiment of the invention. The device 10 comprises a base member or an engineering block 12 to which a flexible link arm 14 is fixed at the free end of which a retaining element 16 for retaining the tissue or organ is provided. The device 10 further includes an adapter unit 18 which is communicated with the engineering block 12 via plural lines 20. A compressed air cartridge 22 serving as external power source and supplying the working medium required for actuating the tightening mechanism for the link arm 14 integrated in the engineering block 12 can be connected to a compressed air connection 24 at the adapter unit 18. Via a compressed air line 20a, the compressed air is transmitted from the adapter unit 18 to the engineering block 12. A signal line 20b extending in parallel thereto serves for controlling the fluid control elements or valves (not shown) provided in the adapter unit 18 which can be controlled by the engineering block 12 and by the link arm 14, respectively.

Figure 2:
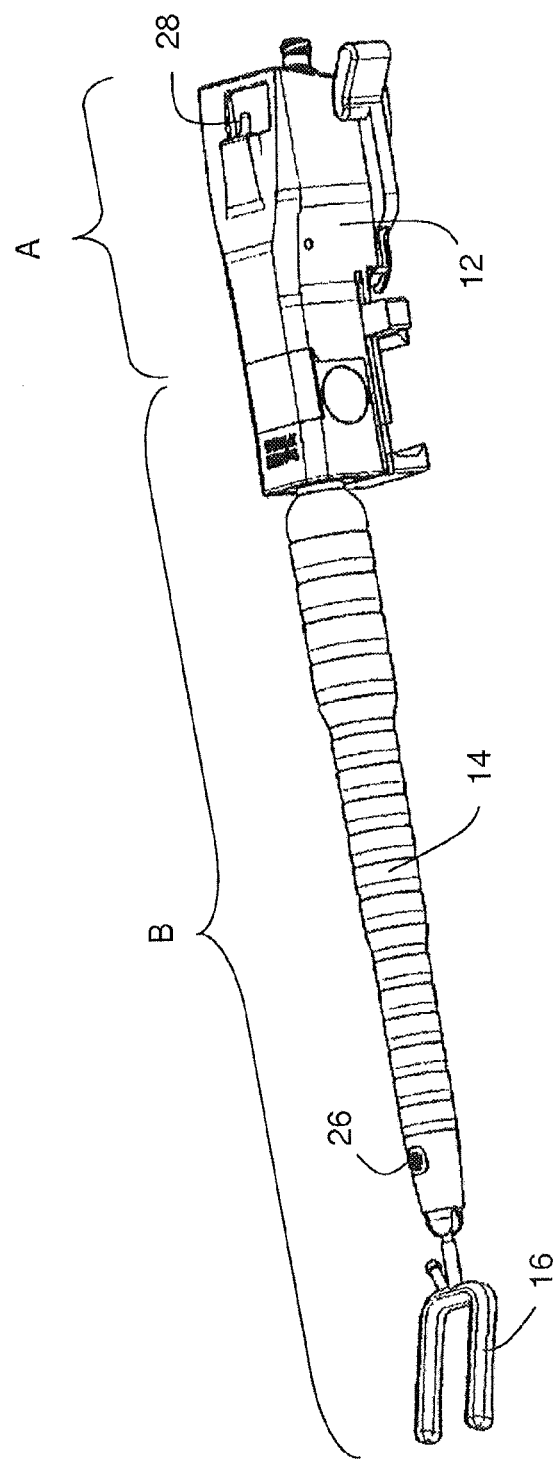
FIG. 2 shows an engineering block including a coupled link arm of the surgical device shown in FIG. 1.

FIG. 2 shows the engineering block 12, the link arm 14 and the retaining element 16 in an enlarged representation. The engineering block 12 substantially contains the entire mechanism for tightening the link arm 14 as well as for fixing the overall system to external supports not shown, such as a sternum spreader. The engineering block 12 constitutes a re-usable engineering module A and the link arm 14 including the retaining element 16 constitutes a working module B designed for single use.

From FIG. 2, it is further evident that at the distal end of the link arm 14 a first actuating element 26 is provided in the form of an electric push-button, and at the engineering block 12 a second actuating element 28 is equally provided in the form of an electric push-button. Both actuating elements 26 and 28 serve for controlling the energy flow from the external power source, i.e. for controlling the compressed air passing from the compressed air cartridge 22 via the compressed air line 20a and a compressed air connection 30 to the engineering block 12. The actuating elements 26, 28 and the control of the external power source can be configured so that the energy flow is released as long as the actuating elements 26, 28 are pressed. Alternatively, the energy flow can be released by once-only actuation and can be suppressed again by second actuation.

Figure 3:
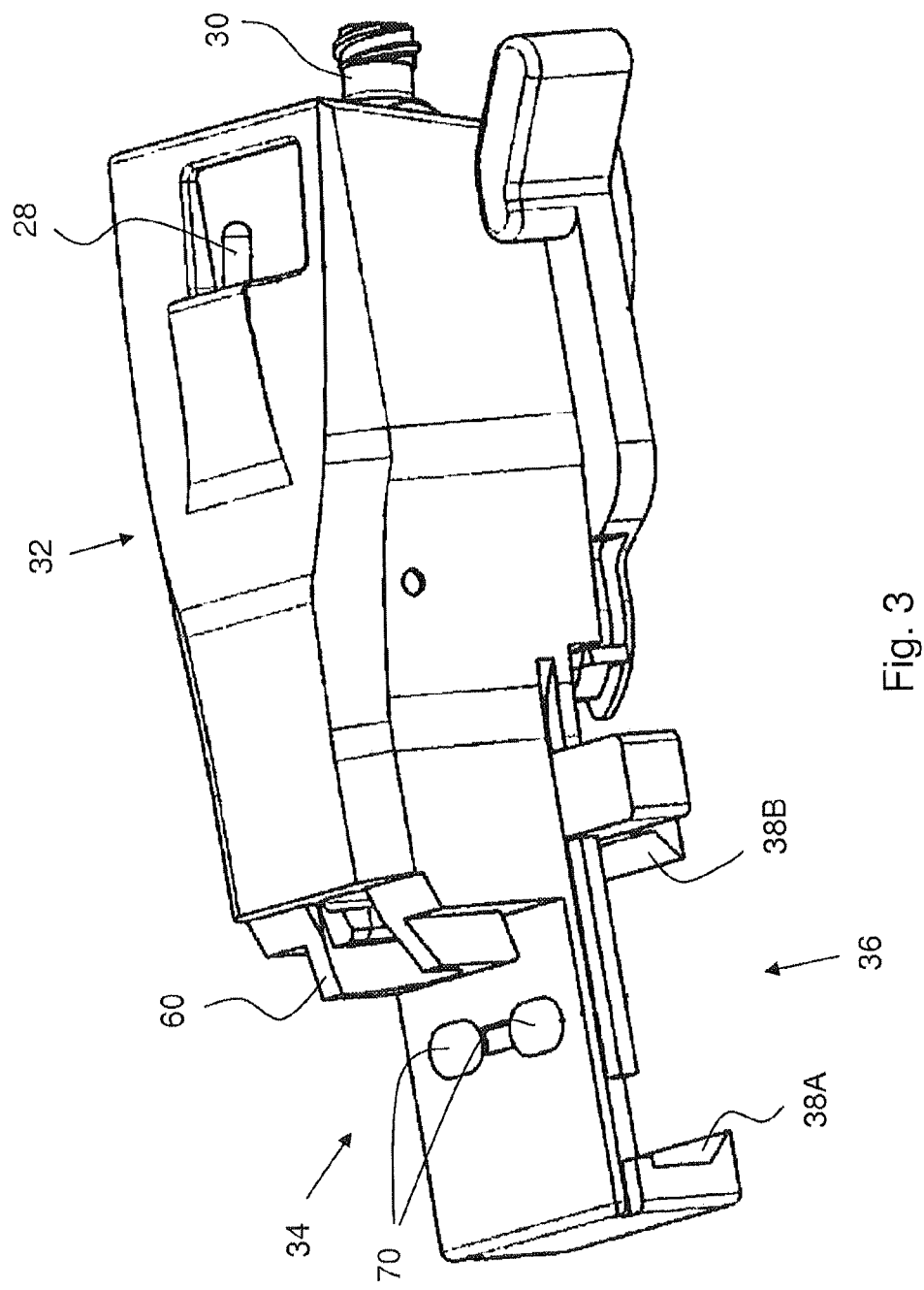
FIG. 3 shows a perspective view of the engineering block.

FIG. 3 illustrates a perspective view solely of the engineering block 12. The engineering block 12 includes a housing portion 32, a coupling portion 34 for coupling the working module B and a fastening portion 36 for fastening the engineering block 12 to a support (not shown), such as a sternum spreader. The housing portion 32 may be provided with ergonomic grip recesses so that mounting and/or dismounting of the working module B can be simplified.

Figure 4:
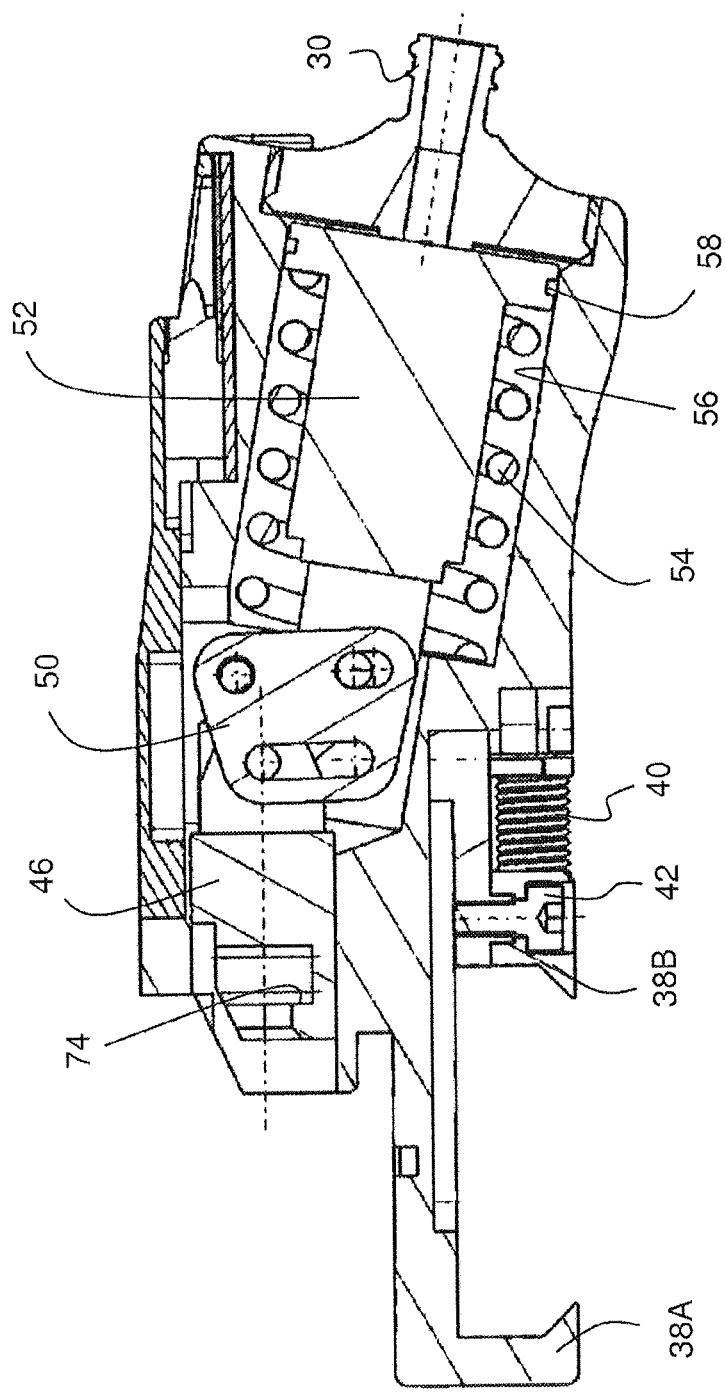
FIG. 4 shows a cross-sectional view of the engineering block shown in FIG. 3.

The fastening portion 36 includes two undercut clamping jaws 38a and 38b widthwise adjustable relative to each other by which the engineering block 12 can be mounted in friction fit and form fit to an appropriate rail or similar holding device. The adjustable clamping jaw 38b is biased via a spring 40 against the fixed clamping jaw 38a, as is evident from FIG. 4. The adjustable clamping jaw 38b can be further fixed via a clamping screw 42.

In the housing portion 32 a cylinder-piston mechanism 44 is provided which constitutes a substantial part of the tightening mechanism. A slide or carriage 46 guided in the housing portion 32 in the axial direction, i.e. in the longitudinal direction of the link arm 14, which is connectable to a pull rope 48 guided in the link arm 14 is pin-jointed to one end of a piston 52 of the cylinder-piston mechanism 44 via an intermediate joint 50 so that a lifting movement of the piston 52 results in a translational axial displacement of the carriage 46.

The piston 52 is biased via a helical compression spring 54 in a direction into which the piston 52 pulls the pull rope 48 via the carriage 46 toward the engineering block 12 and, in this way, braces and fixes or stiffens the link arm, as will be described hereinafter in detail. Due to the spring bias, in the idle state, i.e. without any external intervention, the link arm 14 is present in the fixed or locked state.

In order to be able to bend the link arm 14 which is flexible into any direction, the spring bias must be reversed. This is done by means of an external power source. The piston 52 can be actuated into the opposite direction, against the compression force of the helical compression spring 54 with the aid of compressed air supplied via the compressed air connection 30 to a cylinder chamber 56 of the cylinder-piston mechanism 44, and thus can release or relax the pull rope 48 by appropriately displacing the carriage 46 and thus release the fixed link arm 14.

One or more piston rings 58 ensure the fluid-tight separation of the part of the cylinder chamber 56 pressurized with compressed air from the part of the cylinder chamber 56 in which the helical compression spring 54 is provided. The movement of the piston 52 and the carriage 46 is delimited in both directions by respective stops so as to set defined adjusting travels for releasing and tightening.

Hereinafter, the coupling of the working module B to the engineering module A shall be described in more detail.

The interface between the working module B and the engineering module A does not only serve for purely mechanical, but also for signal-related and functional coupling of the two units, as, on the one hand, the control signals input via the distal actuating element 26 have to be transmitted to the engineering block 12 and from there via the control signal line 20b to the adapter unit 18 by the appropriate control elements and, on the other hand, the pull rope 48 extending within the link arm 14 has to be coupled to the cylinder-piston mechanism 44.

Figure 5:
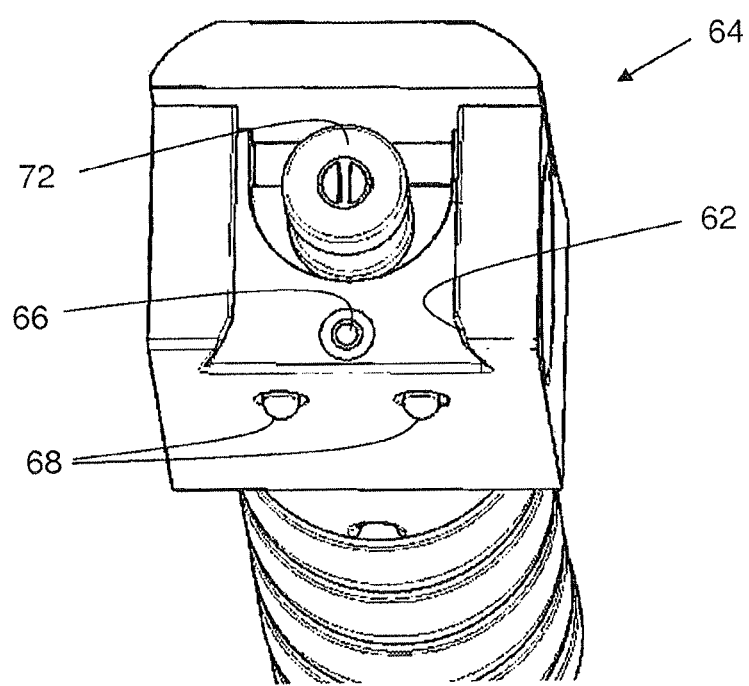
FIG. 5 shows a perspective view of the link arm.

For mechanically coupling the module A to the module B, the coupling portion 34 of the engineering block 12 provided immediately above the fastening portion 36 includes a vertically extending dovetail guide 60 which forms a positive connection to a complementary guide seat 62 at a coupling portion 64 of the working module 8 (cf. FIG. 5). For this purpose, the coupling portion 64 is pushed vertically onto the dovetail guide 60, until the two coupling portions 34 and 64 are in surface contact. For detachably locking the two coupling portions 34 and 64, a locking element 66 is provided at the coupling portion 64 of the working module B in the form of a spring-biased locking lug. Furthermore, at the lower side of the coupling portion 64 two electrical contacts 68 are provided which enter into contact with corresponding contact points 70 at the coupling portion 34 of the engineering block 12, when the two modules A and B are provided in their coupled and locked working position. The electrical contacts 68 are communicated with the distal actuating element 26 via electric lines 90. In the engineering block 12 equally lines (not shown) are provided for connecting the contact points 70 to the outgoing control line 20b.

Furthermore, from FIG. 5 an end piece 72 of the pull rope 48 is evident. The end piece 72 is a rotation-symmetric profiled rotary member which accurately fits in a corresponding recess 74 within the carriage 46 and in this way can be positively connected to the carriage 46 in the axial direction or in the direction of tension. The end piece 72 at the free end of the pull rope 48 further ensures that the pull rope 48 guided through the coupling portion 64 does not unthread.

The end piece 72 can be inserted from above into the recess 74, when the slide 46 is provided in the fully extended position. Since in the idle state the carriage 46 is retracted due to the bias of the spring 54, for inserting the end piece 72 into the recess 74 the carriage 46 has to be extended via the cylinder-piston mechanism 44. By actuating the actuating element 28 at the engineering block 12 compressed air is supplied to the engineering block 12 and the piston 52 is pressurized so that the latter moves toward the link arm against the spring force of the spring 54 (to the left in FIG. 4) and thereby pushes the carriage 46 out of the housing portion 32 so far that the free end of the pull rope 48 or the end piece 72 can be inserted into the recess 74 of the carriage 46. After releasing the actuating element 28 the compressed air supply is suppressed. The helical compression spring 54 moves the piston 52 into its idle position again, which causes the carriage 46 to be retracted along with the end piece 72 of the pull rope 48. By retracting the carriage 46 the pull rope 48 is further tightened and the link arm 14 is fixed and immobilized in its current position. In the retracted position the carriage 46 is located inside the housing portion 32 so far that the end piece 72 is secured in the recess 74 of the carriage 46.

Figure 6:
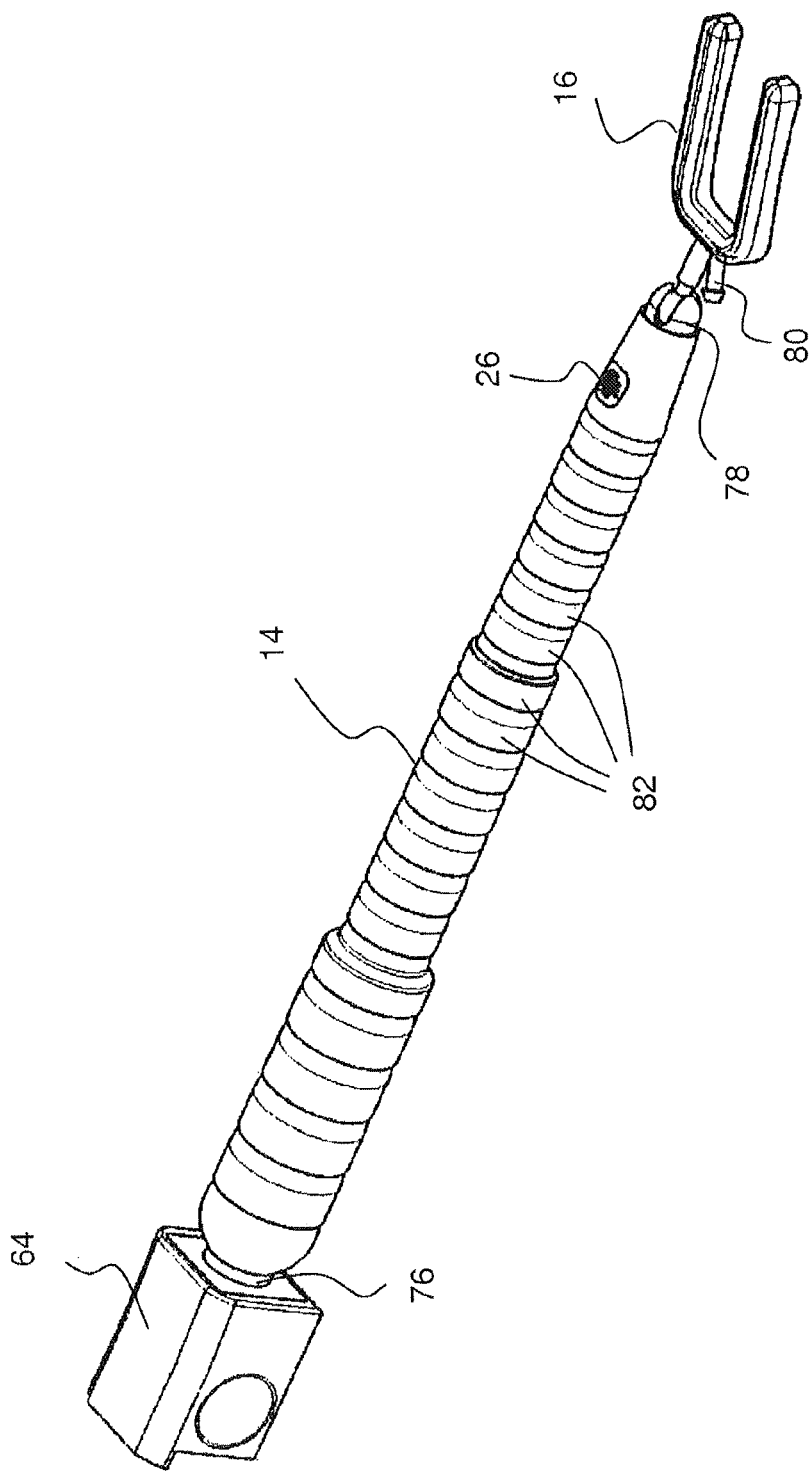
FIG. 6 shows an enlarged view of a proximal portion of the link arm.

FIG. 6 illustrates the entire working module B consisting of the coupling portion 64, a proximal joint 76, the actual link arm 14, the distal actuating element 26 arranged at the distal end of the link arm 14, a distal pivot joint 78 and the retaining element 16. The proximal (spherical) joint 76 permits rotation of the link arm 14 about the longitudinal axis relative to the coupling portion 64 and furthermore a pivoting movement of the link arm 14 so the link arm 14 can be lowered vertically into the patient's body cavity. The distal pivot joint 78 enables a pivoting movement of the retaining element 16 relative to the distal end of the link arm 14. The retaining element 16 can be in the form of a vacuum-assisted stabilizing or positioning element, for example. If it is a stabilizing element, the vacuum-assisted U-shaped member is locked together with the link arm 14 as soon as tensile force is applied to the pull rope 48. The working ends of the retaining element 16 are usually made of soft materials so as to perfectly adapt to the tissue or else to anatomic conditions and thus admit as little leakage of the vacuum as possible. The retaining element 16 can suck onto the tissue and/or the organ by means of vacuum. For providing the vacuum the retaining element 16 includes a connection 80 so that the retaining element 16 can be pressurized with vacuum via a vacuum line not shown here. In a different embodiment, the retaining element 16 can be provided with a universal adapter so as to allow the connection of most various single-use or re-usable surgical instruments and apparatuses which are held and positioned by means of the link arm 14 during surgical intervention.

Figure 7:
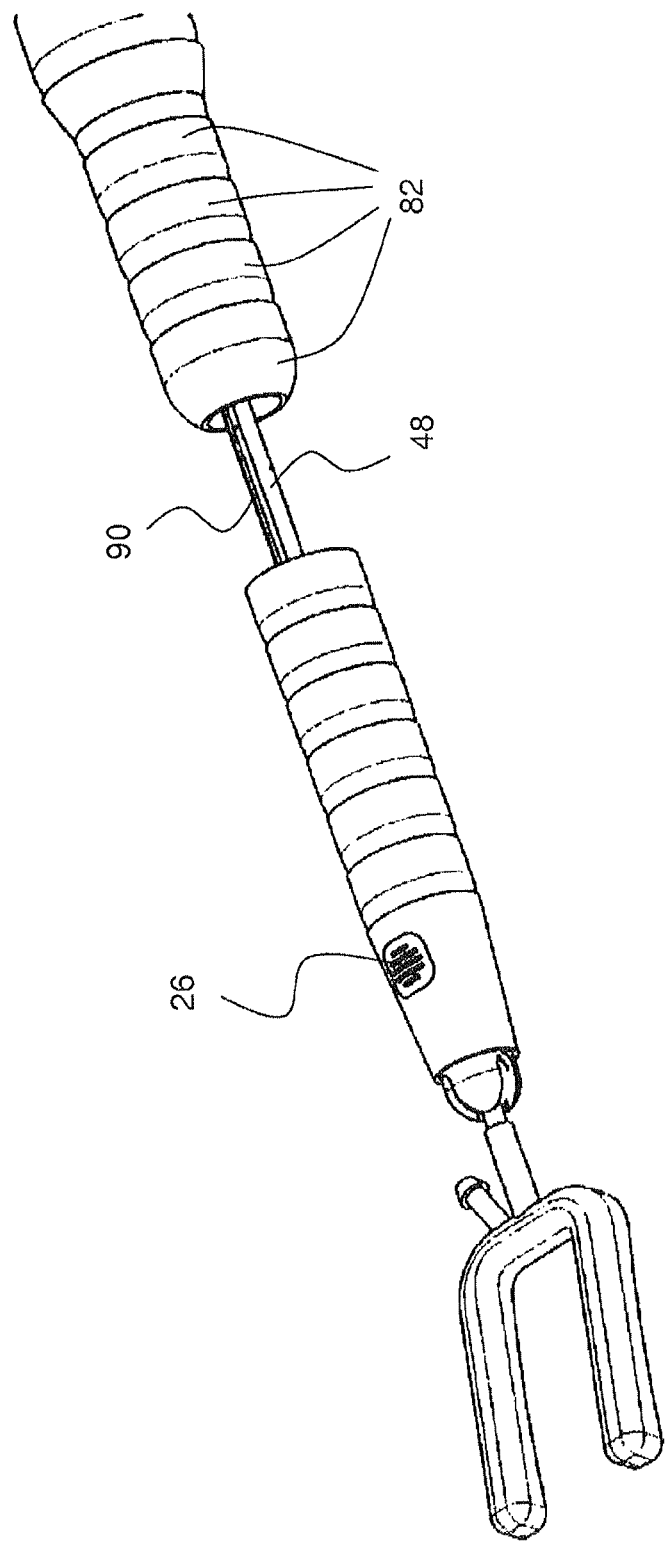
FIG. 7 shows an enlarged partial view of the proximal portion of the link arm.

A pull rope 48 extends through the link arm 14, as shown in FIG. 7 in which some of the link elements 82 of the link arm 14 are missing for reasons of illustration. The flexible link arm 14 consists of a plurality of rotation-symmetric individual link elements 82 which are identical except for the magnitude and act like a plurality of strung spherical joints. The link elements 82 substantially take the shape of a spherical sleeve or a spherical calotte having a central through-hole 84, a distal spherical outer surface 86 and a proximal spherical inner surface 88. Adjacent link elements 82 contact each other at said spherical surface portions 86, 88 and are kept in contact via the pull rope 48.

The link elements 82 can be inexpensively manufactured, e.g. by injection molding. For this, very stiff materials have to be provided with respect to compression. In order to increase the friction coefficient between the link elements 82 sliding against each other also combinations of materials can be used. In particular, the spherical surfaces 86, 88 slipping against each other can be appropriately coated.

The link elements 82 can be braced against the first link element 82 and the proximal joint 76 on the proximal side via the pull rope 48 centrally passed through which is coupled to the last link element 82 and the distal pivot joint 78 on the distal side. By the force fit or friction fit between the spherical surfaces 86, 88 the individual link elements 82 can be fixed at almost any position relative to each other, thus enabling the link arm 14 to be fixed or stiffened. At the same time, the proximal joint 76 and the distal joint 78 are locked in this way. If, on the other hand, the pull rope 48 is relaxed, the friction fit between the individual link elements 82 is disconnected so that they slip against each other again and can move relative to each other.

Furthermore, from FIG. 6 it is evident that the link elements 82 at the proximal end of the link arm 14 are larger than the link elements 82 at the distal end of the link arm 14. This is due to the following reason. The more distally a link element 82 is located, the lower is the bending moment acting upon occurrence of transverse force on said link element 82. Since, when a transverse force is introduced at the arm, the bending moment is highest at the proximal link elements 82, i.e. at the link elements having the largest distance from the distal end, said link elements will firstly displace against each other. By appropriately selecting different diameters of the link elements 82 according to the course of the bending moment to be expected a uniform bending of the arm can be achieved.

The distal actuating element 26 configured as an electric push-button in this embodiment is connected via two electric lines 90 which are equally guided through the inside of the link elements 82 and which transmit the input control signals to the electrical contacts 68 in the coupling portion 64. Since the lines 90 extend inside the link elements 82, they are protected against external influences. However, care has to be taken that the lines 90 are not injured or damaged by the movement of the individual link elements 82 and the pull rope 48, respectively.

Figure 8:
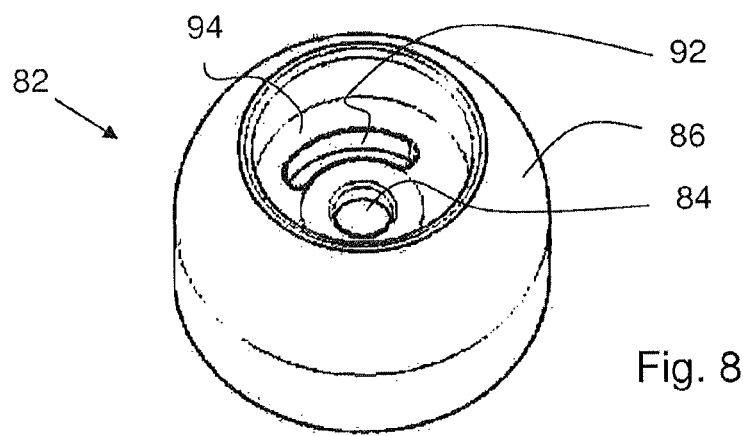
FIG. 8 shows a perspective view of an individual link element according to a first embodiment of the invention.

Against this background, as is shown in FIG. 8, the individual link elements 82 include, apart from the central through-hole 84 for the pull rope 48, one or more eccentrically arranged recesses 92 through which power transmission lines 90 such as hoses, cables or the like extend protected against the movement of the parallel pull rope 48.

Figure 9:
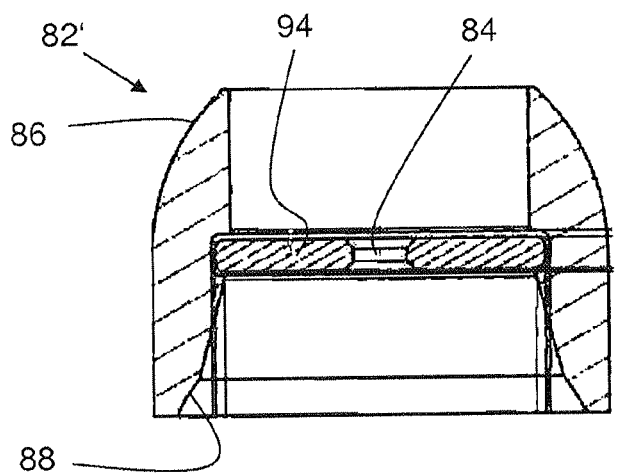
FIG. 9 shows a perspective view of an individual link element according to a second embodiment of the invention.

Since the individual link elements 82 cannot only be shifted or tilted laterally relative to each other but can also be twisted against each other, this might result in twisting and possibly damage of the lines 90. Against this background, in the link elements 82' according to a second embodiment illustrated in FIG. 9 the central through-hole 84 and the recesses 92 for the lines 90 are provided in a rotary disk 94 accommodated in the link elements 82' to be rotatable about the longitudinal axis. Said rotary disks 94 thus can compensate for a twisting of the link elements 82.

Figure 10:
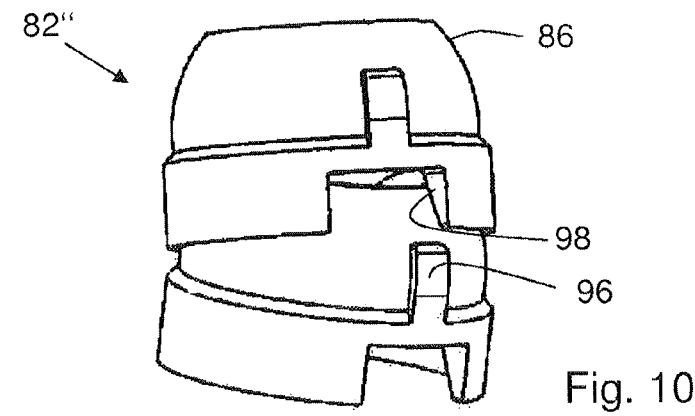
FIG. 10 shows a perspective view of two link elements according to a third embodiment of the invention.

A third embodiment of the link elements 82" is illustrated in FIG. 10. FIG. 10 shows two link elements 82" provided with positive engaging elements 96, 98 for an anti-twist protection of the link elements 82". The engaging elements 96, 98 on the one hand are projections 96 formed in the area of the spherical outer surface 86" and, on the other hand, are break-outs 98 in the area of the spherical inner surface 88", with the projections 96 engaging in the break-outs 98. As is evident from FIG. 10, the width of the break-outs 98 is larger than that of the projections 96 so that a certain rotatory degree of freedom is admitted and the projection 96 can move somewhat in the direction of rotation inside the break-out 98.

Figure 11:
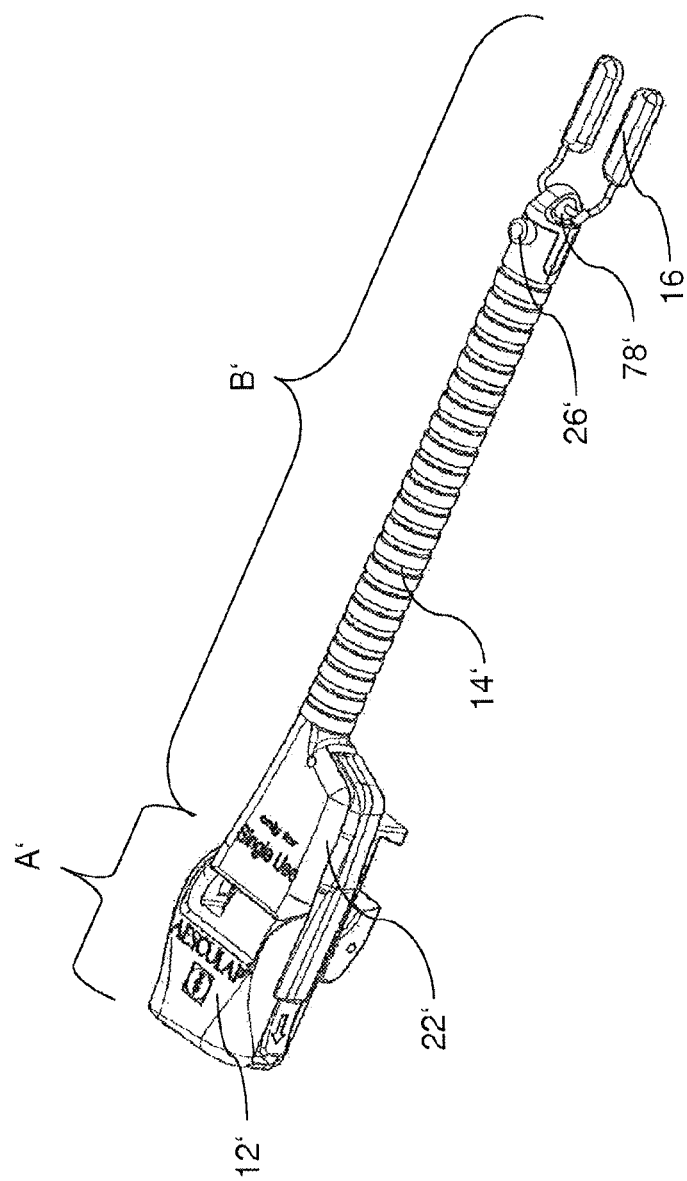
FIG. 11 shows a perspective view of a surgical device according to a fourth embodiment of the invention.

FIG. 11 illustrates a perspective view of the surgical device 10' according to a fourth embodiment of the invention. The most crucial difference from the afore-described embodiments consists in the integral incorporation of the power source in the form of an integrated compressed air cartridge 22' in the enlarged coupling portion 64' of the link arm 14'.

In the functional respect, the coupling portion 64' on the one hand ensures the same coupling capability of the link arm 14' and of the engineering block 12' with respect to the pull rope 48' and the cylinder-piston mechanism 44' and with respect to the end piece 72' and the recess 74' as well as with respect to the electrical contacts 68' and the contact points 70' as the link arm 14 and the engineering block 12 according to the first embodiments of the invention. On the other hand, however, a surgical device 10' according to the fourth embodiment moreover also includes components at the link arm 14' and at the engineering block 12' which ensure the connection of the integrated compressed air cartridge 22' to the cylinder-piston mechanism 44'.

The concrete configuration of the fourth embodiment differs in the distal area of the working module B' as to the realization of the pivot joint 78' between the fork-like retaining element 16' and the link arm 14' to the effect that the pivot axis extends in a way twisted orthogonally compared to the first embodiments. Hence, pitching of the retaining element 16 instead of yawing is admitted.

For easier handling the distal actuating element 26' is raised or exposed with respect to the direct vicinity of the actuating element 26'.

In contrast to the first three embodiments, the outer dimensions of the link elements 82''' of the link arm 14' of the fourth embodiment do not vary over the length of the link arm 14'. In order to still obtain a uniform flexibility of the link arm 14' corresponding to the course of the bending moment respective taper angles α (cf. FIG. 9) of the link elements 82''' are gradually (i.e. individually adapted for each link element 82''') or in portions (i.e. for adjacent link elements 82''' equal in one portion of the link arm 14') increased from the engineering block 12' toward the retaining element 16.

Figure 12A:
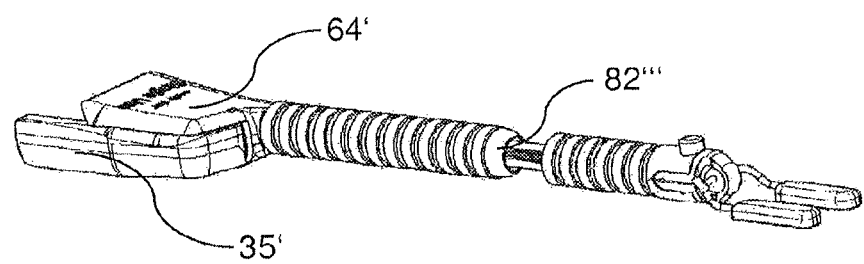
FIG. 12a shows a perspective front view of the link arm of the surgical device according to a fourth embodiment.
Figure 12B:
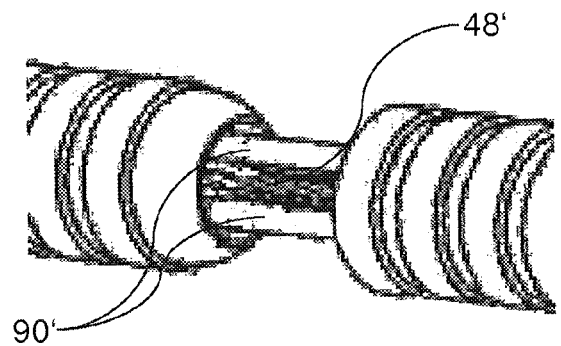

As is shown in FIGS. 12a and 12b, in which individual link elements 82''' are not shown for illustration purposes, the pull rope 48' extends in the center of the link arm 14' and three electric lines 90' uniformly distributed over the circumference of the pull rope 48' extend inside the link arm 14'.

In the area of the coupling portion 64' of the working module B' which is aligned with the link arm 14' both the pull rope 48' and the electric lines 90' are guided from the front side of the coupling portion 64' starting from the link arm 14' toward the rear side of the coupling portion 64' to the corresponding connections of the electrical contacts 68' and the end piece 72'.

The end piece 72' is T-shaped, with the cross beam of the T-shaped end piece 72' preferably being transverse to the direction in which the coupling portion 64' of the working module B' is inserted into the coupling portion 34' of the engineering module A' during assembly.

Figure 13A:
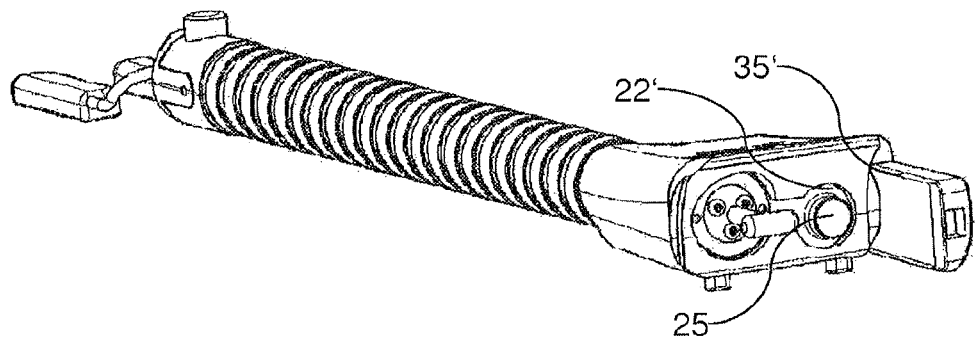
FIG. 13a shows a perspective rear view of the link arm of the surgical device according to the fourth embodiment.
Figure 13B:
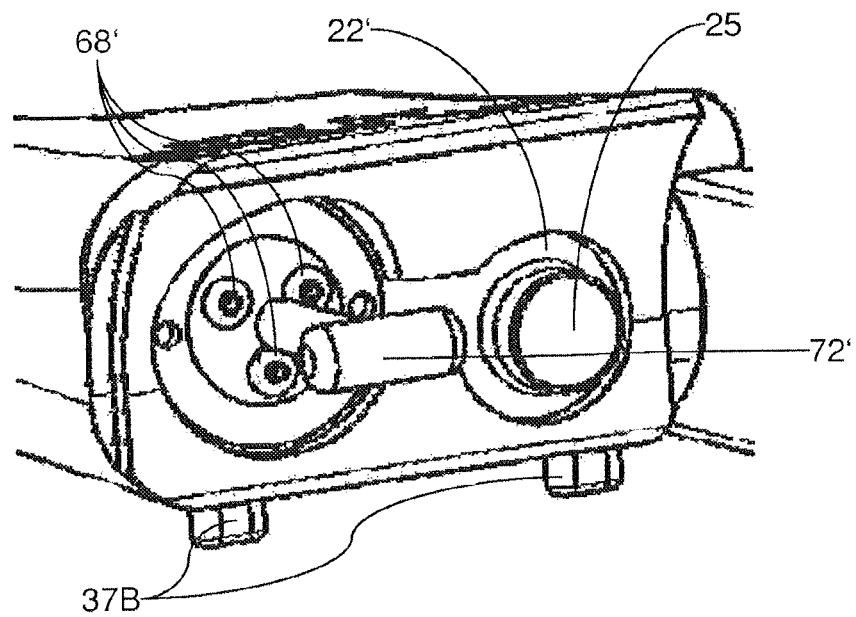

In the area of the coupling portion 64' of the working module B' which is not aligned with the link arm 14', the integrated compressed air cartridge 22' is accommodated. As is evident from FIGS. 13a and 13b, the compressed air cartridge 22' is arranged in the coupling portion 64' of the working module B' such that at the rear side of the coupling portion 64' a connection of the compressed air cartridge 22' in the form of a sealing membrane 25 is accessible. The compressed air cartridge 22' can be moved axially, i.e. substantially perpendicularly or transversely to the rear side surface of the coupling portion 64' by pivoting a connecting lever 35.

The rear side surface of the coupling portion 64' is formed or curved to be circular-cylindrical so that in the lower area it extends substantially perpendicularly to the linearly aligned link arm 14' and in the upper area it extends at an angle thereto.

On the lower side of the coupling portion 64' in the vicinity of the rear side surface of the coupling portion 64' two coupling projections 37B are downwards projecting.

Figure 14:
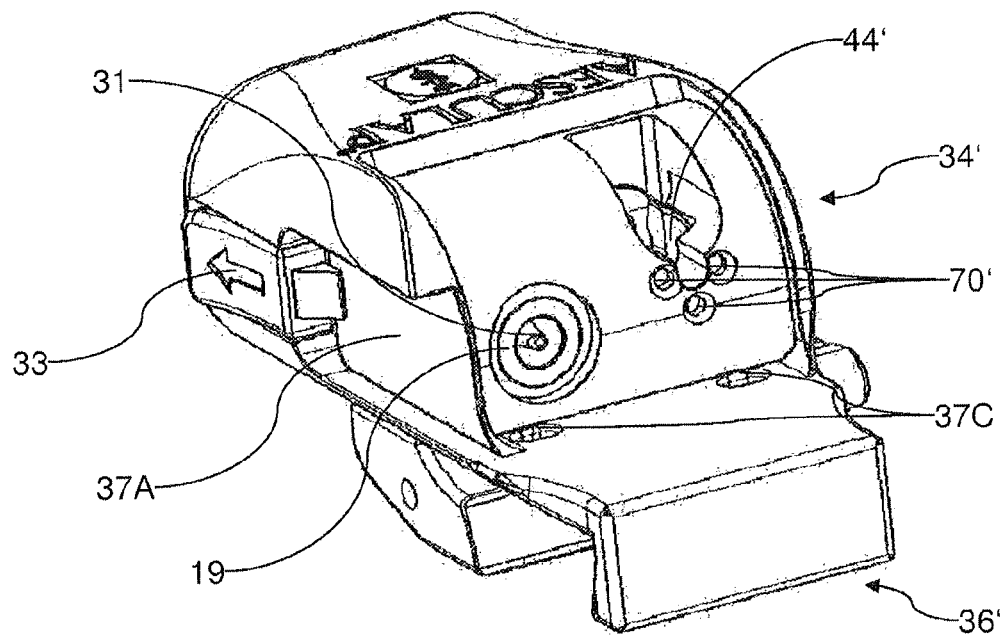
FIG. 14 shows a perspective front view of the engineering block of the surgical device according to a fourth embodiment.

FIG. 14 illustrates a perspective view of the front side of the engineering module A' of the surgical device 10' according to the fourth embodiment to which the rear side of the working module B' is adapted to be coupled.

Corresponding to the area of the coupling portion 64' of the working module B' aligned with the link arm 14', connections are provided in the area of the coupling portion 34' of the engineering module A' aligned with the link arm 14' in the form of the contact points 70' and in the form of the recess 74', which connections are connected to the electrical contacts 68' and the end piece 72' during mounting of the working module B' to the engineering module A'.

On the front side of the area of the coupling portion 34' of the engineering module A' which is not aligned with the link arm 14' a compressed air connection including a piercer 31 and a pressure control unit 19 is arranged.

The fastening portion 36' of the engineering module A' substantially corresponds to the fastening portion 36 of the first three embodiments, but projects to the front so that the coupling portion 64' of the working module B' does not only contact the front side of the engineering module A' but also rests on parts of the upper side of the fastening portion 36' of the engineering module A'. Two coupling recesses 37C are provided on the upper side of the fastening portion 36'.

On the side of the engineering block A' a lever recess 37A is shaped so that the connecting lever 35 pivoted to the working module B' can be folded into the lever recess 37A only when the engineering module A' and the working module B' are provided at a defined position relative to each other for coupling. In order to lock the connecting lever in its folded position a locking slide 33 is provided for arresting the connecting lever 35.

The front side surface of the coupling portion 34' of the engineering module A' is adjusted to the rear side surface of the coupling portion 64' of the working module B' and hence exhibits substantially the same circular-cylindrical curvature as the rear side surface of the coupling portion 64'.

Figure 15:
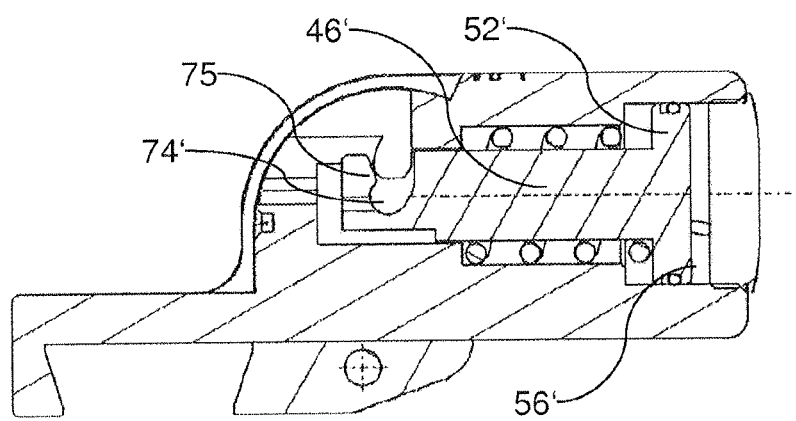
FIG. 15 shows a cross-sectional view of the engineering block shown in FIG. 14.

FIG. 15 illustrates a cross-sectional view of the engineering block 12' of the surgical device 10' according to the fourth embodiment. As is also illustrated by a comparison with FIG. 4, in the fourth embodiment the slide 46' and the piston 52' are formed coaxially and in one piece. In accordance with this embodiment, a connecting intermediate joint 50 is not required.

The recess 74' in the slide 46' includes a clamping lug 75 which is shaped so that, when the end piece 72' is inserted into the recess 74', the cylinder-piston mechanism 44 can be displaced by insertion of the piston 52' in the axial direction. When the end piece 72' is inserted in the recess 74', the cylinder-piston mechanism 44' is displaced toward the link arm 14' up to a particular turning point while simultaneously overcoming the force exerted by the helical compression spring 54, before the cylinder-piston mechanism 44' is displaced away from the link arm 14' after overcoming the turning point with the aid of the force exerted by the helical compression spring 54. Hence by means of the clamping lug 75 the tension of the link arm 14' can be generated already during assembly of the working module B'. The clamping lug 75 can be shaped so that the end piece 25 can be removed from the recess again only after adjusting the cylinder-piston mechanism 44' by actuating the distal actuating element 26', i.e. that thus the end piece 72' is prevented from being removed by self-locking. Otherwise the recess 74' can also be shaped, as is shown in FIG. 15, so that the tension of the helical compression spring 54 can be overcome by merely lifting the coupling portion 64' of the working module B' and in this way the end piece 72' of the recess 74' can be removed. In this case the drivability of the tightening mechanism (44', 48') with the aid of the power source in the form of the compressed air cartridge 22' only serves for adjusting the link arm 14' in a mounted state.

The assembly of the device 10 according to the invention in accordance with the first three embodiments is as follows:

First, the engineering block 12 is connected to the adapter unit 18 via compressed air line 20a and signal line 20b. The compressed air source, e.g. a compressed air cartridge 22, is connected to the adapter unit 18. Then the engineering block 12 is fastened to a support in the vicinity of the operation site, e.g. to a sternum spreader, via the fastening portion 36. After that or already before the working module B is connected to the engineering module A and the engineering block 12. For this, the proximal actuating element 28 is pressed so that the carriage 46 travels out of the housing portion 32. When the coupling portion 64 of the working module B is connected to the coupling portion 34 of the engineering module A, the dovetail guide 60 and the seat 62 establish a form closure between the two modules A and B. Furthermore, the electric connection between the contacts 68 and 70 is made. Moreover, the pull rope 48 is coupled to the cylinder-piston mechanism 44, as when sliding on the coupling portion 64 the projecting end piece 72 of the pull rope 48 is simultaneously inserted in the appropriate recess 74 of the carriage 46. If the proximal actuating element 28 is released again, the carriage 46 retracts into the housing 32 again and in so doing tightens the pull rope 48 and fixes the link arm 14 as well as the retaining element 16 at their respective positions and attitudes.

The assembly of the device 10 according to the invention in accordance with the fourth embodiment is as follows:

At first the engineering block 12' is fastened via the fastening portion 36' to a support in the vicinity of the operation site, e.g. to a sternum spreader. After that or already before that, the working module B' is connected to the engineering module A' and to the engineering block 12'. For this purpose, the proximal end of the link arm 14' or the coupling portion 64' is guided with the connecting lever 35 in its opened position toward the coupling portion 34' of the engineering block 12' so that the coupling projections 37B enter into the coupling recesses 37C.

As can be inferred from FIG. 15, the end piece 72' of the pull rope 48' simultaneously enters into the recess 74' of the cylinder-piston mechanism 44'. The clamping lug 75 causes the end piece 72' to be pulled into the proximal direction when entering into the recess 74' and thus the link arm 14' to be tightened.

The connecting lever 35 cannot be pivoted into the dedicated lever recess 37A and thus into its closed position before the coupling portion 64' of the working module B' is provided at the stop with the opened connecting lever 35 after the coupling projections 37B have entered into the recesses.

The integrated compressed air cartridge 22' is arranged in the proximal end of the link arm 14' such that the connection thereof points toward the engineering block 12' during assembly of the link arm 14'. The compressed air connection of the integrated compressed air cartridge 22' is formed by the sealing membrane 25 which has to be pierced for the supply of compressed air from the integrated compressed air cartridge 22' to the engineering block 12'. Once the membrane 25 has been pierced, the integrated compressed air cartridge 22' cannot be closed again to be airtight any more, or at least not without considerable effort, let alone be refilled with compressed air.

In the fourth embodiment of the invention, the membrane 25 is perforated with the aid of the movable piercer 31 arranged at the coupling portion 34' of the engineering block 12'. If the coupling portion 64' of the link arm 14' and the coupling portion 34' of the engineering block 12' are provided at a dedicated position relative to each other, the distance between the piercer 31 and the membrane 25 can be reduced by means of the connecting lever 35 until the collision and thus the perforation take place.

The connecting lever 35 can be provided at the link arm 14' as depicted and merely the integrated compressed air cartridge 22' and thus the membrane 25 can be moved toward the piercer 31. Alternatively, it would also be possible to provide the connecting lever 35 at the engineering block 12', to render only the piercer 31 movable in the direction of the membrane 25 or to render both the piercer 31 and the membrane 25 movable.

The connecting lever 35 does not only ensure that the membrane 25 is perforated, but also that the connection of the integrated compressed air cartridge 22' to the cylinder-piston mechanism 44' is realized via the pressure control unit 19.

Immediately before the membrane 25 is perforated, the area around the perforation site is sealed to the outside. This is achieved by the fact that the components provided for sealing and the components configured to be movable for perforating the membrane 25 (membrane 25 and/or piercer 31) are differently supported so that both the components provided for sealing and the components designed to be movable for perforating the membrane 25 can be controlled by the connecting lever 35, but that the components provided for sealing are leading over the components designed to be movable for perforating the membrane 25.

The operating mode of the device 10 according to the invention is as follows:

By actuating the distal actuating element 26, the compressed air valves in the adapter unit 18 or in the engineering block 12 are controlled by appropriate electric signals. The compressed air valves in the first three embodiments pressurize the piston 52 in the engineering block 12 via the compressed air lines 20a and relax the pull rope 48. In this way the operating surgeon can grip the link arm 14 at the distal end by one hand, appropriately deform it and guide the retaining element 16 into the body cavity toward the tissue to be stabilized or the organ to be retained. If the operating surgeon releases the distal actuating element or repeatedly actuates the same, the external energy supply to the tightening mechanism and the compressed air supply to the cylinder-piston mechanism 44 is suppressed and the tightening mechanism is tightened again via the helical compression spring 54 and thereby the link arm 14 and the retaining element 16 are fixed or immobilized in their current position.

By repeated actuation of the distal actuating element 26 or the proximal actuating element 28, the tightening mechanism can be released again for readjusting or removing the link arm 14 from the body cavity.

If in a surgical device 10' according to the fourth embodiment the link arm 14' is dismounted again after the first mounting, the opening of the connecting lever 35 causes the sealing of the connection of the membrane and the pressure control unit to be initially abandoned. Thus the residual compressed air not used before escapes from the integrated compressed air cartridge 22'. Consequently, the link arm 14' cannot be adjusted any more by means of the cylinder-piston mechanism 44' after second mounting and thus loses most of its functionality.

However, the present invention is not restricted to the embodiments described in detail before but can be varied within the scope of protection of the attached claims. Hereinafter several such variation possibilities are listed.

Instead of the modular design of the working module B and the engineering module A, the latter can be designed in one part and as a whole can be provided as a single-use component. In this way all interfaces between the two units and the related operating steps for connecting are dropped. This concept in turn can be implemented either with only one, ideally distally arranged actuating element or with two actuating elements for controlling the external energy flow.

In accordance with the first embodiment, the compressed air originates from a compressed air cartridge 22 permitting completely autonomous working. Instead of the compressed air cartridge 22, a compressed air hose can be connected to the compressed air connection 24 of the adapter unit 18 and can be linked with any other compressed air source, e.g. a given air supply in the operating theater.

The energy transmission lines 90 between the distal actuating element 26 and the engineering block 12 can also extend outside the link arm 14. The vacuum line to the retaining element 16 can equally extend inside the link arm 14, wherein appropriate interfaces between the modules A and B and lines and connections have to be provided in the engineering block 12 in that case.

The fluid control elements in the adapter unit 18 can also be controlled pneumatically instead of electrically, the compressed air piston 52 being operated with the working medium air, e.g. at a pressure of 8 bars, while the valve releasing the energy flow can be controlled with considerably lower pressure. Said low pressure in turn provides for more flexible control lines having thinner walls and a by far compacter actuating element.

The fluid control elements may also be provided in the engineering block 12 and the compressed air source may be directly connected to the engineering block 12.

The invention describes a surgical device for stabilizing or immobilizing moving tissue or for positioning organs, especially a part of a beating heart, comprising a flexible arm 4', especially a link arm, fixed or fixable to a base member which arm can be brought into different positions and/or attitudes. At least one retaining element 16 is arranged at the free end of the arm. The surgical device also includes a tightening mechanism 44, 48; 44', 48' by which the arm can be fixed at a desired position. The tightening mechanism 44, 48; 44', 48' is tightened and/or released by means of a manually controllable external power source 22; 22'.

The invention claimed is:
1. A surgical device for stabilizing or immobilizing moving tissue, or for positioning organs or for positioning and holding surgical instruments and apparatuses during surgical intervention, comprising:
a base member adapted to be fastened to a retaining device provided in or at an operation site by a fastening portion;
a flexible arm adapted to be fastened to the base member which arm can be brought into different positions and/or attitudes and at a free end of which at least one retaining element is arranged; and
a tightening mechanism by which the arm can be fixed in a desired position and which includes:
a pull rope which is guided through a plurality of link elements of the arm that are movable relative to one another and by which the link elements can be frictionally braced against each other; and
an actuating mechanism for actuating the pull rope, wherein the surgical device has a modular design and the arm is mechanically connectable to and disconnectable from the base member without using tools,
the tightening mechanism is automatically tightened by a spring mechanically coupled to the pull rope to exert tension force on the pull rope, and the tightening mechanism is released by means of a power source through which the actuating mechanism can be actuated, and
the actuating mechanism comprises a setting element which can be brought into an extended position by means of the power source so that, when a mechanical connection between the arm and the base member is made, at the same time the pull rope is coupled to the setting element of the actuating mechanism.

2. The surgical device according to claim 1, wherein the power source is outside the base member.

3. The surgical device according to claim 1, wherein the power source can be controlled via at least one actuating element which is manually operable and arranged on a distal and/or proximal side of the arm and/or on the base member.

4. The surgical device according to claim 3, wherein
the power source is a hydraulic or pneumatic pressure source or an electric power source;
the actuating mechanism is a cylinder-piston mechanism to be actuated hydraulically, pneumatically or by an electric motor; and
a fluid control valve for controlling a fluid pressure acting on the cylinder-piston mechanism or an electric control device for controlling an electric power acting on the electric motor for moving the cylinder-piston mechanism can be controlled via the at least one actuating element.

5. The surgical device according to claim 4, wherein each of the link elements includes a central pull rope passage for the pull rope and at least one eccentrically arranged recess for a control line between the at least one actuating element and the fluid control valve or the electric control device.

6. The surgical device according to claim 5, wherein the central pull rope passage and the at least one recess are provided in a rotary disk rotatably supported in the link element or
the link elements include an anti-rotation protection comprising engaged locking elements so as to restrict twisting of the link elements around the pull rope.

7. The surgical device according to claim 4, wherein between the at least one power source and the base member an adapter unit is interconnected which is connected via detachable lines on one side to the base member and on an opposite side to the at least one power source.

8. The surgical device according to claim 7, wherein the fluid control valve or the electric control device is arranged in the adapter unit.

9. The surgical device according to claim 1, wherein
the power source in the form of a self-sustained energy storage unit can be detachably inserted in the arm or is integrated in the same so that, when the mechanical connection is made between the arm and the base member, at the same time the base member and the energy storage unit are interconnected.

10. The surgical device according to claim 9, wherein
the energy storage unit is fixedly integrated in the arm, wherein the arm is designed for single use and the energy stored in the energy storage unit can only be used and/or is designed only for a period of use between a first coupling of the arm to the base member and a first decoupling of the arm from the base member.

11. The surgical device according to claim 1, wherein the retaining element is provided with a universal adapter.

12. A surgical working arm for being arranged on a base member of a surgical device according to claim 1 to be fastened to a retaining device provided in or at an operation site by a fastening portion for stabilizing or immobilizing moving tissue or for positioning organs the working arm comprising:

a flexible link arm adapted to be brought into different positions which includes a plurality of strung link elements movable relative to one another and formed to be complementary;

at least one retaining element arranged at a distal end of the link arm; and a coupling portion for mechanical and functional connection of the working arm to the surgical device, wherein a pull rope which is guided through the link elements and by which the link elements can be frictionally braced against each other includes a proximal connecting portion which can be connected to and disconnected from a tightening mechanism provided in the surgical device without using tools.

13. The surgical working arm according to claim 12 comprising:

an actuating element provided at the distal end of the link arm for controlling the tightening mechanism provided in the surgical device; and control lines extending inside the link arm which connect the actuating element to interfaces provided in the coupling portion for transmission of control signals or instructions to the surgical device.

14. The surgical working arm according to claim 12, wherein the retaining element is provided with a universal adapter.

15. The surgical working arm according to claim 12, wherein an energy storage unit can be detachably inserted into the working arm or is integrated in the same, such that, when a mechanical and functional connection of the working arm to the surgical device is made, the surgical device can be supplied with energy from the energy storage unit.

* * * * *